United States Patent [19]

Nicolson et al.

[11] Patent Number: 5,164,489

[45] Date of Patent: Nov. 17, 1992

[54] LUNG GROWTH STIMULATORY AND INHIBITORY FACTORS FOR CARCINOMA TUMOR CELLS

[75] Inventors: Garth L. Nicolson, Kingwood; Philip G. Cavanaugh, Houston, both of Tex.

[73] Assignee: Board of Regents, University of Texas System, Austin, Tex.

[21] Appl. No.: 197,689

[22] Filed: May 23, 1988

[51] Int. Cl.$^5$ ............ C07K 15/14; C07K 15/28
[52] U.S. Cl. ................ 530/397; 530/399; 530/395; 530/388.24; 530/389.2
[58] Field of Search ........... 530/397, 399, 395, 350, 530/387

[56] References Cited

U.S. PATENT DOCUMENTS 4,670,539 6/1987 Sirbasku.

OTHER PUBLICATIONS

Cavanaugh et al. 1989, Cancer Research 49:3928-3933.
Campbell, A. M. 1985, Monoclonal Antibody Technology, In Laboratory Techniques in Biochemistry and Molecular Biology, (eds.) Burdon et al. Elsevier, New York, pp. 66-254.
Abstract, Biosir Number 70001775 of Naum et al. 1979 Inflammation 3(3): 253-260.
Cavanaugh et al., Proceedings of American Association for Cancer Research Annual Meeting, 29:71 (1988).
Nicolson et al., J. Cell Biochem, Suppl. (1989).
Nicolson, Biological Abstracts, 83:10, No. 98591 (1987).
Macaulay et al., Chemical Abstracts 108:148083y (1988).
Nicolson, Garth L., "Differential Growth Properties of Metastatic Large-Cell Lymphoma Cells in Target Organ-Conditioned Medium"; 168 Esp. Cell Res. 572-577 (1987).
Szaniawska, Bozena, et al., "Stimulatory and Inhibitory Activities of Lung-Conditioned Medium on the Growth of Normal and Neoplastic Cells in Vitro"; 75 JNCI no. 2, 303-306 (Aug. 1985).
Kirk, David et al., "Modulation of Growth of a Human Prostatic Cancer Cell Line"; 41 Cancer Research 1100-1103 (Mar. 1981).
Nicolson, Garth L. et al., "Organ Specificity of Metastatic Tumor Colonization is Related to Organ-Selective Growth Properties of Malignant Cells"; 38 Int. J. Cancer, 289-294 (1986).

Primary Examiner—Robert A. Wax
Assistant Examiner—Keith C. Furman
Attorney, Agent, or Firm—Arnold, White & Durkee

[57] ABSTRACT

The invention relates to the purification and characterization of growth stimulatory and inhibitory protein factors produced by various organs which appear to play a role in the successful formation of metastatic colonies of tumor cells. In particular, it has been found that syngeneic organs secrete protein growth stimulatory and inhibitory factors which can, at low concentrations, affect metastatic tumor cells. The ability of a malignant cell to respond to these factors is believed to be related to tumor cell metastasis to specific body organs. In particular a lung growth stimulatory glycoprotein having a molecular weight of approximately 66,000 daltons has been found to stimulate growth of lung-metastatic rat and human mammary tumor cells in serum deprived medium.

6 Claims, 8 Drawing Sheets

Fig. 3 CONCANAVALIN-A AGAROSE

Fig. 4 SEPHACRYL S-200

| STEP | TOTAL PROTEIN (ug) | TOTAL UNITS | UNITS/ UG | PERCENT RECOVERY |
|---|---|---|---|---|
| COND MEDIA | 238400 | 274800 | 1.15 | |
| HYDROXYAPATITE | 58000 | 80000 | 1.38 | 29 |
| DEAE SEPHAROSE | 32000 | 39000 | 1.25 | 14.6 |
| CHROMATOFOCUSING | 4700 | 11000 | 4.00 | 3.6 |
| GEL FILTRATION | 930 | 6840 | 7.60 | 2.5 |
| PREPARATIVE ELECTROPHORESIS | 90 | 8800 | 23.00 | 3.2 |

LUNG GROWTH STIMULATORY AND INHIBITORY FACTORS FOR CARCINOMA TUMOR CELLS

The invention relates to the purification and characterization of growth stimulatory and inhibitory protein factors produced by various organs which appear to play a role in the successful formation of metastatic colonies of tumor cells. In particular, it has been found that syngeneic organs secrete protein growth stimulatory and inhibitory factors which can, at low concentrations, affect metastatic tumor cells. The ability of a malignant cell to respond to these factors is believed to be related to tumor cell metastasis to specific body organs. In particular a lung growth stimulatory glycoprotein having a molecular weight of approximately 66,000 daltons has been found to stimulate growth of lung-metastatic rat and human mammary tumor cells in serum deprived medium.

BACKGROUND OF THE INVENTION

The study of the factors which enable malignant tumor cells to metastasize to various organs is one of the most active fields of cancer research. To block the metastatic spread of cancer by arresting growth of micrometastases would be of tremendous clinical value. Certain types of tumor cells are known to show preferences in their ability to metastasize to certain organs (Nicolson and Poste, Int. Rev. Exp. Pathol. 25:77–81, 1983). In animal tumor systems, tumor cells sublines can be selected that metastasize preferentially to specific organ sites (Nicolson, Hospital Pract. 17(8): 75–86, 1982). One of the more recently developed hypotheses concerning this phenomenon is that a target organ secretes particular growth factors to which a particular type of tumor cell is responsive (Nicolson and Dulski, Int. J. Cancer 38:289–294, 1986; Horak, et al., J. Nat'l. Cancer Inst. 76:913–922, 1986, Nicolson, Exp. Cell. Res. 168:572–577, 1987). Thus, the development of a metastatic lesion by a malignant cell in a specific organ is promoted by a proper growth environment (Nicolson, Cancer Res 47:1473–1487, 1987).

Evidence to support this theory has been published in several studies which demonstrate that certain murine B16 melanoma sublines and murine RAW117 large cell lymphoma/lymphosarcoma sublines express an accelerated growth response in culture when exposed to medium conditioned by the organ that they preferentially metastatize to. (Nicolson and Dulski, Int J. Cancer 38:289–294, 1986, Nicolson, Exp. Cell. Res. 168:572–577, 1987). Other investigators have noted that a series of murine colon adenocarcinoma cell lines can demonstrate growth responsiveness towards lung homogenates which positively correlates with the lines ability to metastasize to the lung (Tsuruo, et al., Clin. Exptl. Met. 4:25–331, 1986; Yamori, et al., Clin. Exptl. Met. 6:131–139, 1988. Certain organ conditioned media can increase the growth rate of tumor cells in culture (Horak, et al., J. Nat'l. Cancer Inst. 76:913–922, 1986; Szanlawska, et al., J. Nat'l Cancer Inst. 75:303–306, 1985).

Tumor cells are known to respond to a wide variety of defined growth factors (Goustin, et al., Cancer Res. 46:1015–1029, 1986). For example, tumor cell responsive to epidermal growth factor has been studied by several laboratories (Goustin, et al., Cancer Res. 46:1015–1029, 1986; Singletary, et al., Cancer Res. 47:403–406, 1987; Spitzer, et al., Int. J. Cancer 39:279–282, 1987; Ozawa, et al., Int. J. Cancer 39:333–337, 1987). Fibroblast growth factor (Richmond, et al., Cancer Res. 42:3175–3180, 1982) and platelet derived growth factors (Hara, et al., Cancer Res. 46:1212–1216, 1980) have also been found to stimulate the growth of certain tumor cells. The ability to respond to transforming growth factors is thought to enable tumor cells to grow in an anchorage-independent state (Goustin, et al., Cancer Res. 46:1015–1029, 1986). Certain tumor cells possess the ability to secrete their own growth factors (autocrine growth factors) to which they can themselves respond (Sporn and Roberts, Nature 373:745–747, 1985; Richmond and Thomas, J. Cell. Phys. 129:375–384, 1986).

Partial purification of tumor growth factors from the normal tissues in which they arise, has been accomplished by a few investigators (Ikeda and Sirbasku, J. Biol. Chem. 259:4049–4064, 1984; Miyzawa, et al., Leukemia Res. 9:1315–1321, 1985; Spies, et al., Biochem Biophys. Res. Commun. 138:795–802, 1986). However, many of these factors may never be released from the tissue cells under normal conditions. This is different than the current approach which is to isolate the organ cell secreted factors from tissues where the tumor cells metastasize to because it is believed that these substances are secreted by the organ cells in vivo and are important in metastatic tumor spread to distant organ sites.

The organ derived growth factors that have been detected in the work described above have for the most part not been purified and/or characterized. Recently however, a novel lung growth factor for the highly metastatic MTLn3 mammary adenocarcinoma tumor line from lung-conditioned medium has been derived and characterized.

SUMMARY OF THE INVENTION

The present invention provides a class of peptide growth factors derivable from lung tissue (LGF1). One of the growth factors of this invention is a Mr. 66,000 glycoprotein. Chromatofocusing of the protein has shown it to have a PI of 6.9–7.0. The molecular weight of the protein increases slightly following reduction with Mercaptoethanol to between 72,000–74,000 daltons. Further characterization of these factors indicates that glycosylation is present. Cleavage with cyanogen bromide under non-reducing conditions produces two fragments having molecular weights of 39,000 and 29,000 daltons. Finally, the growth factors of the invention exhibit increased biological activity in high metastasizing epithelial cell lines. This is to be distinguished from epithelial growth factor which has a lower molecular weight of 15,000–18,000 daltons and does not distinguish between high and low metastasizing cell lines. The growth factors of the present invention exhibit no biological activity in low metastasizing cell lines.

The source materials for the growth factors are lung tissues which are dissected free of major bronchioles. Rat, porcine and human lung tissue have been used as source tissues. Activity from all three sources have been found to be the same and the purified material from both migrates to the same position on SDS PAGE gels.

By methods provided by this invention, the growth factors are purified to substantial homogeneity. Substantial homogeneity as used herein is 95% or greater purity of the growth factor so that essentially all of the protein content is responsible for the assessed biological growth activity.

The growth factor is purified to substantial homogeneity from lung tissues by a 7 step method comprising (1) extracting and culturing lung tissue, (2) separating the culture media from the tissue cells, 3) fractionating the medium on a hydroxylapatite affinity column 4) further factionating the active fraction by anion exchange chromatography, 5) affinity chromatography on immobilized Concanavalin −A, 6) subjecting the active fraction to size exclusion chromatography on a Sephacryl S 200 column, and 7) collecting the active fraction from the above step and subjecting it to phenyl sucrose fast protein liquid chromatography column. Other purification steps can include the use of a fast protein liquid chromatography anion exchange using a mono-Q resin.

BRIEF DESCRIPTION OF THE DRAWINGS

FIGS. 6 and 7 ilustrate the ability of LGF-1 to augment the growth of certain tumor cell ines, but not others. In all cases, 2000 cells were seeded onto 96 well microtiter plates in media (alpha-MEM for MTPa, MTC, MTLn3 or DMEM/F12 for MCF7, A375) containing 1% v/v fetal calf serum. 24 hours after plating, the media was replaced with 100 uL media containing 0 3 % v/v fetal calf serum. Approximately 5 units of LGF-1 in a 25 uL volume was then placed into test wells (result bars marked by a +) and 25 uL control solution was placed into control wells (bars denoted by a −). Four days later, relative cell numbers were quantitated and expressed as absorbance at 590 nm using the crystal violet assay described previously. Bars represent the mean ± SD from six wells. With the rat mammary adenocarcinoma system, only the highly metastatic MTLn3 line exhibited a positive response. The low metastic MTPa and MTC lines did not. With human cell lines, the MCF7 mammary adenocarcinoma line responded whereas the A375sm melanoma line did not.

FIG. 11 shows the results of a silver stained 12% acrylamide gel run according to Laemmli (Nature 227:680–685, 1970). Standard bands (lane 1) are slightly obscured. Their running positions are labelled to the left of the gel. Lane 3 received 1 ug of reduced LGF-1 purified by preparative native gel electrophoresis (band 3 from FIG. 9). Lanes 8 and 9 received 1 and 0.2 ug, respectively, of non-reduced protein from the same sample.

DETAILED DESCRIPTION OF THE PREFERRED EMBODIMENT OF THE INVENTION

Figure 1A:
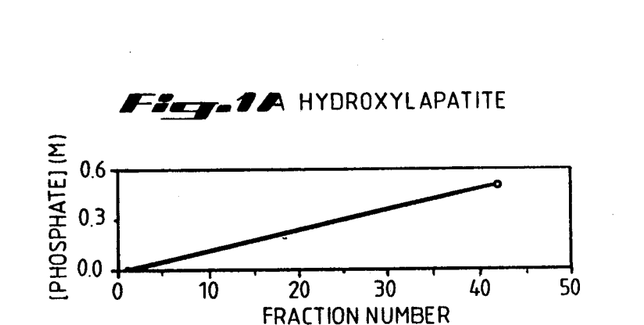
FIG. 1A and FIG. 1B show the elution profile of growth factor activity from hydroxylapatite during the first step of purification. The column was equilibrated with a 10 mM potassium phosphate buffer (pH 7.0). The column was eluted using a 10–500 mM linear phosphate gradient. Each fraction was assayed for growth factor activity by placing 25 microliters of the media fraction into the assay described below. Protein was monitored at 280 nM.
Figure 1B:
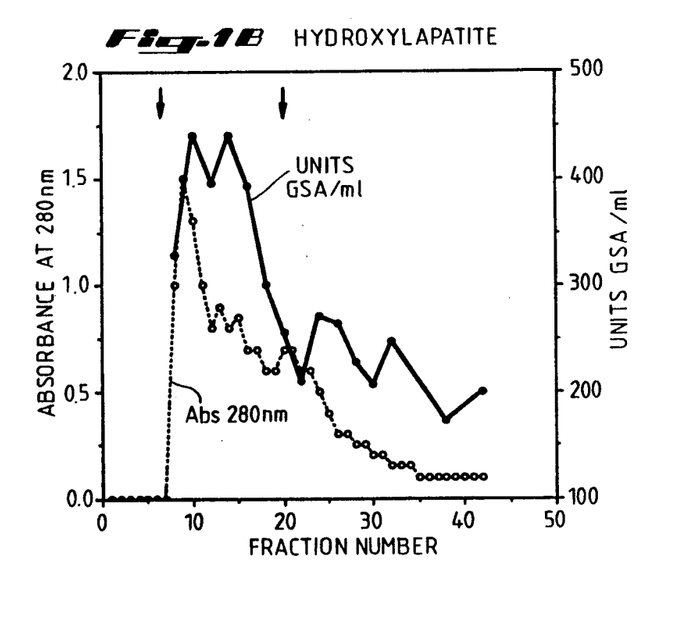
Figure 2A:
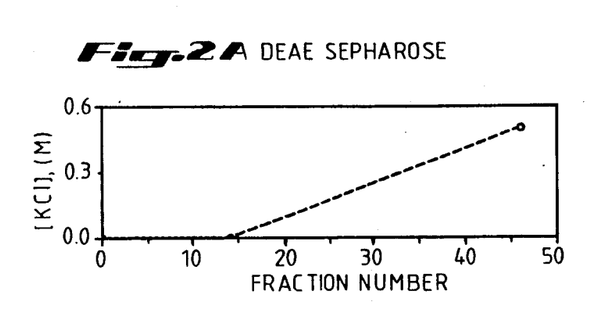
FIG. 2A and FIG. 2B show the elution profile of the active growth factor fractions from step 1 on a DEAE sepharose column. Following dialysis of the active fraction against 25 mM TRIS buffer (pH of 8.5). The bound proteins were eluted from the column using a 0–0.5M KCl linear gradient in a 25 mM TRIS buffer Fractions again were monitored for protein content at 280 nm and the active fractions were also monitored.
Figure 2B:
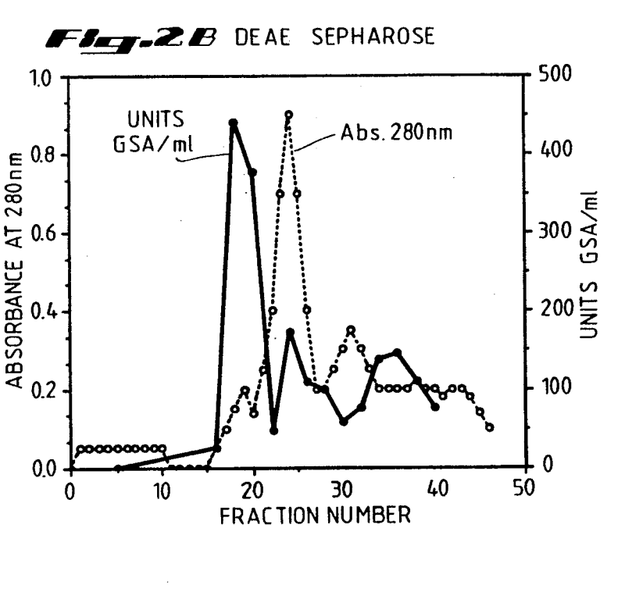
Figure 3:
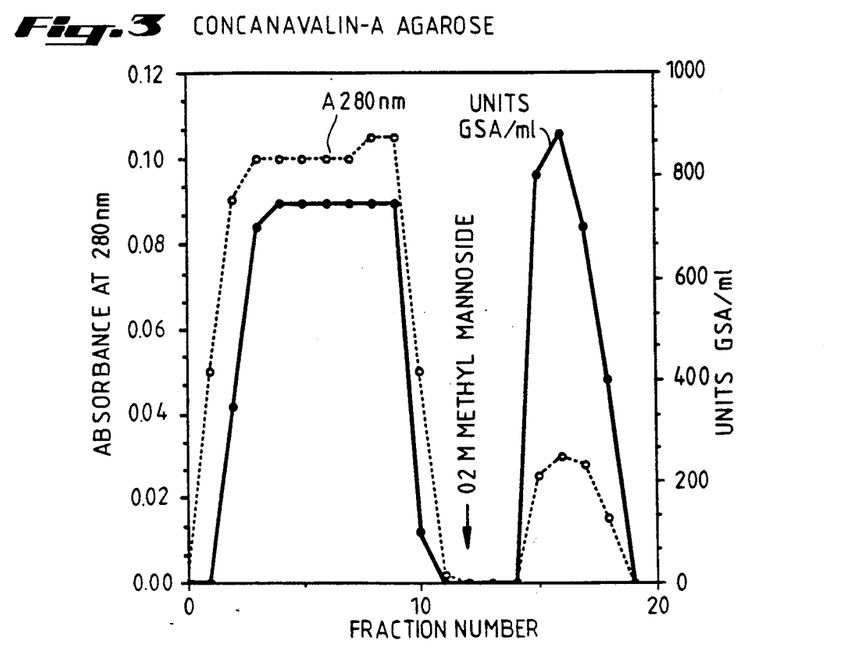
FIG. 3 shows the elution profile of growth factor activity from the concanavalin-A agarose affinity column following dialysis of the active pool from step 2 against a 25 mM phosphate buffer (pH 7.0). The bound proteins were eluted from the column with a starting buffer containing 0.2M α-methyl-D-manoside.
Figure 4:
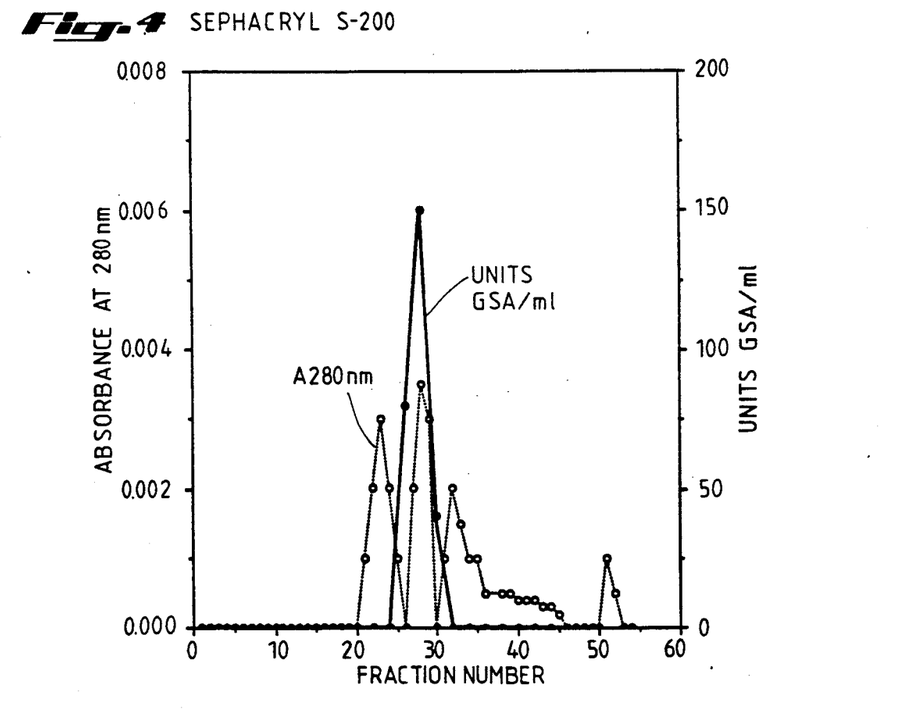
FIG. 4 shows the elution profile of the growth factor activity from Sephcryl S-200 system during step 3 of purification. The column was equilibrated and run at a flow rate of 20 ml per hour with a 50 mM potassium phosphate buffer at a pH of 7 0 containing 0.2M KCl and 0.05% $NaN_3$. Again the fractions were monitored for protein content at 280 nM and the activity of the fractions was measured.
Figure 5A:
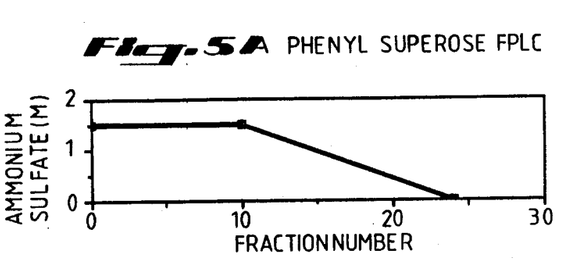
FIG. 5A and FIG. 5B show active fractions from step 4 that made 1.7M in ammonium sulfate that were dialyzed and applied to a phenyl superose FPLC column. Bound proteins were eluted with a 1.7 to 0.0M ammonium sulfate gradient The collected fractions were again monitored for absorbance of 280 mM and for growth promoting activity.
Figure 5B:
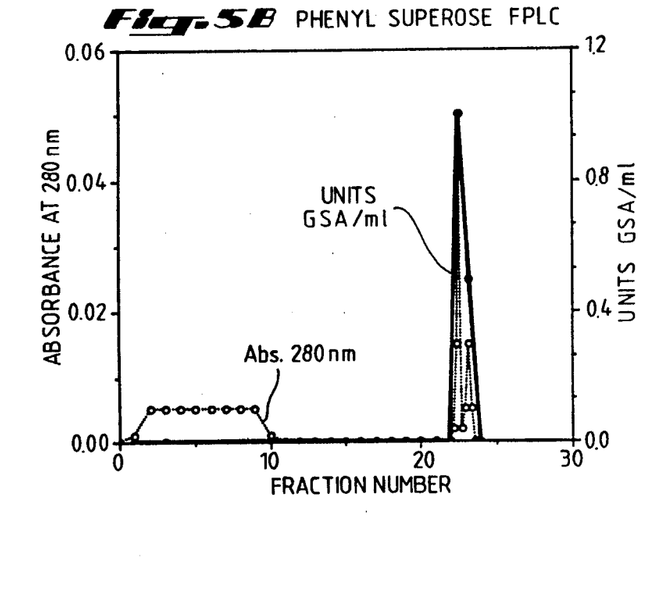
Figure 6:
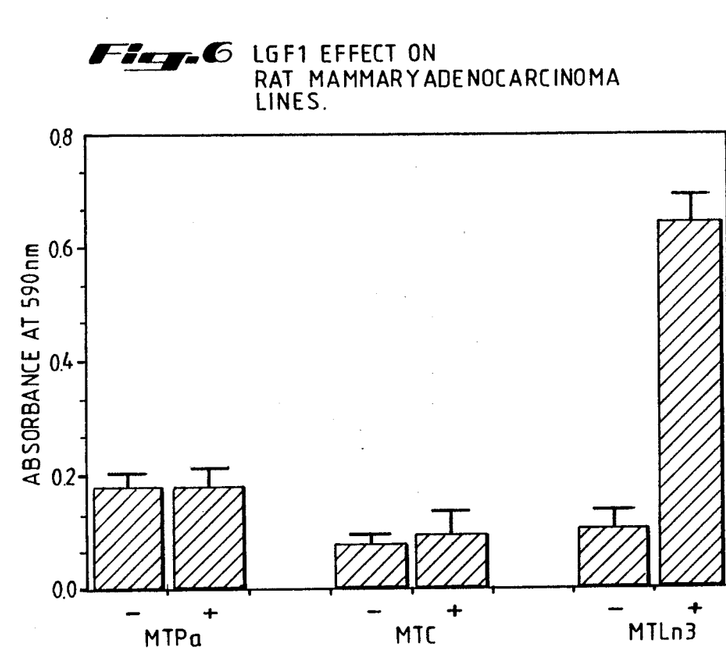
Figure 7:
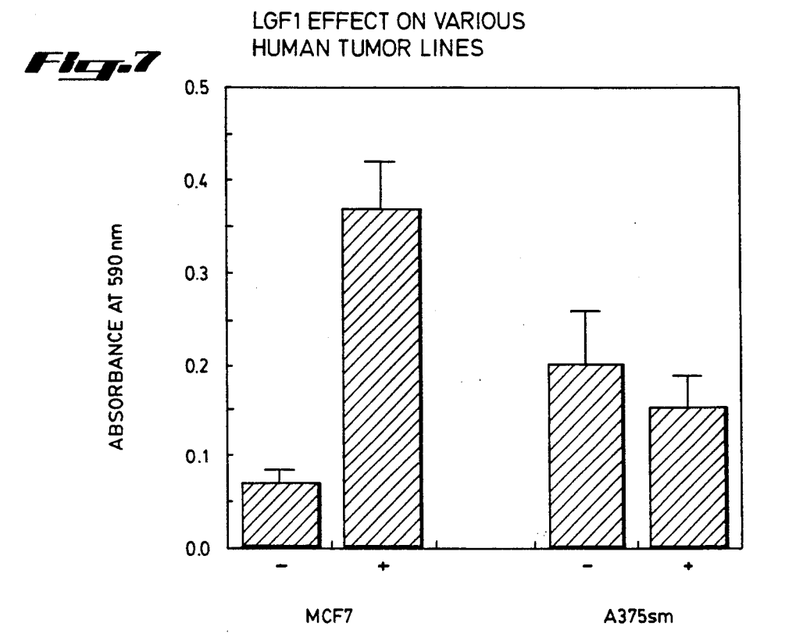
Figure 8:
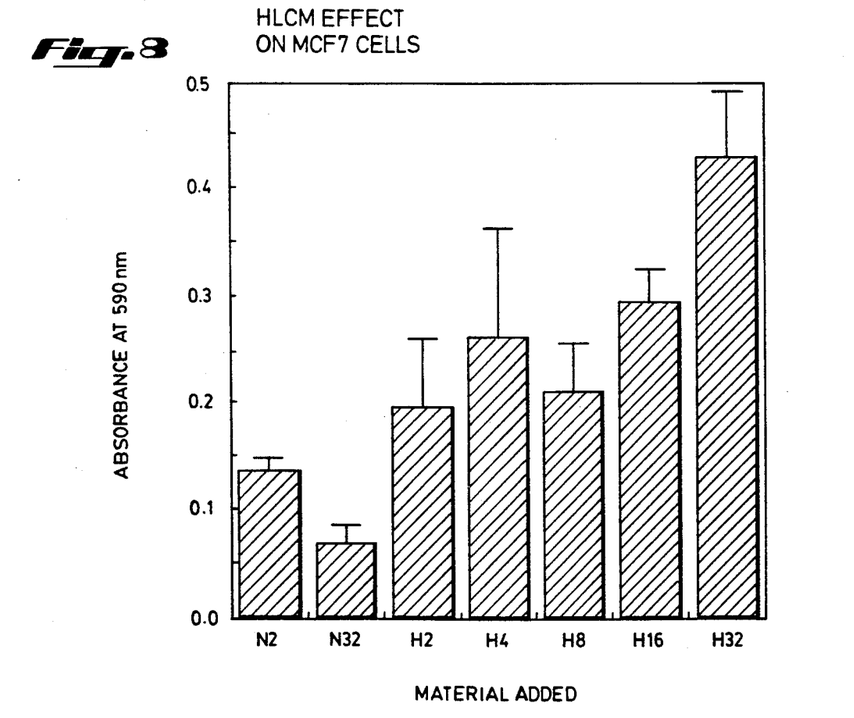
FIG. 8 demonstrates the growth enhancing activity of human lung conditioned media (HLCM) on MCF7 human mammary adenocarcinoma cells. HLCM was prepared using a piece of normal human lung obtained from surgery. The same procedure described for rat and porcine LCM's was employed. Assays were performed as described in the legend for FIGS. 6 and 7. Wells whose result bars marked N2 and N32 received a negative control solution: 2 and 32 uL, respectively. Wells whose result bars are marked by H2, etc., received human lung conditioned media: the number following the H indicating the number of microliters of conditioned media added. Bars represent the mean ± SD for four wells. Wells receiving 32 uL conditioned media contained approximately 5.5 times the number of cells as in the corresponding negative control.
Figure 9A:
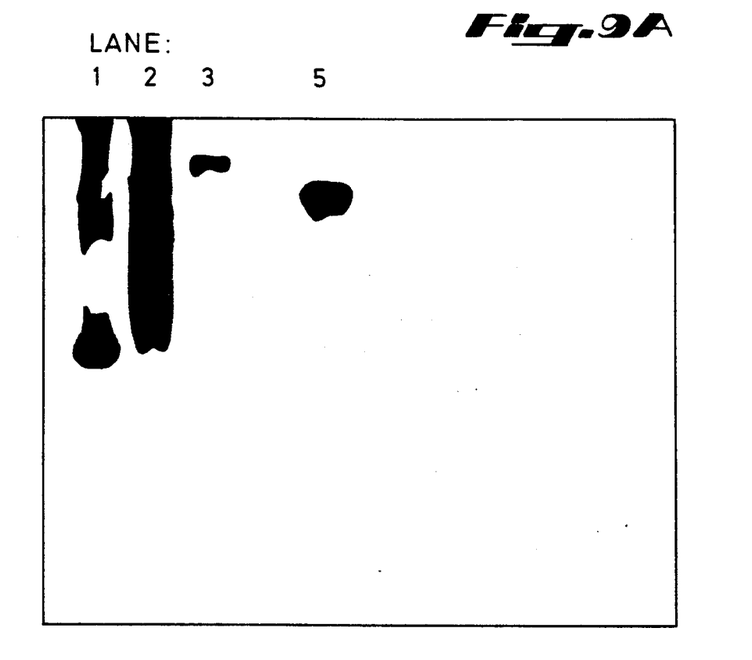
FIG. 9A, lane 5 shows the results of silver staining a native gel loaded with 2 ug of a rat LFG-1 from the Sephacryl 200 active pool. Lanes 1–3 are standards: lane 1 was loaded with bovine serum albumin; lane 2 with alcohol dehydrogenase and lane 3 with yeast amylase.
Figure 9B:
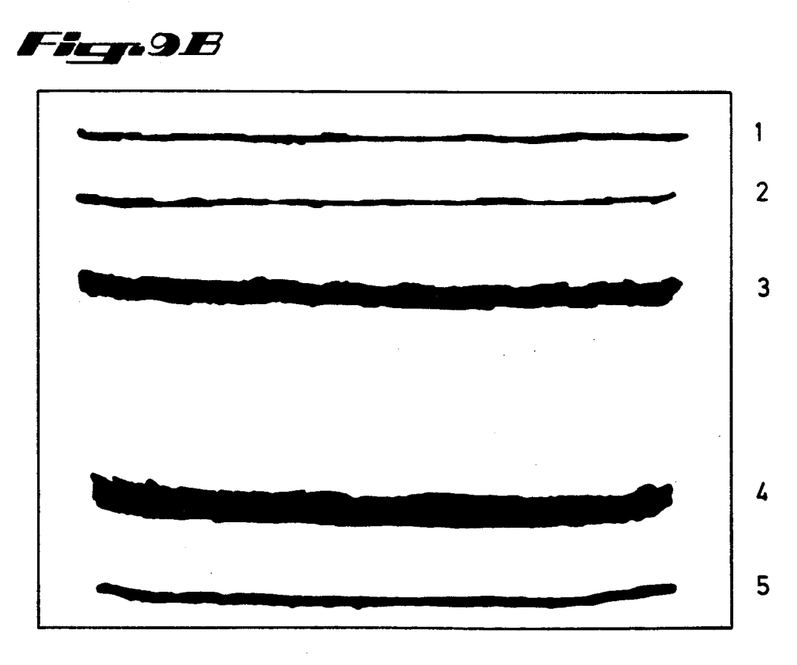
FIG. 9B is an illustration of the appearance of a negative stained preparative native gel loaded with 100 ug of a crude LGF-1 sample. Five bands were observed, and are labeled 1 through 5, from top to bottom. Each band was cut out of the gel with a scalpel, the proteins within were electroeluted and assayed for growth stimulating activity on MTLn3 cells.
Figure 10:
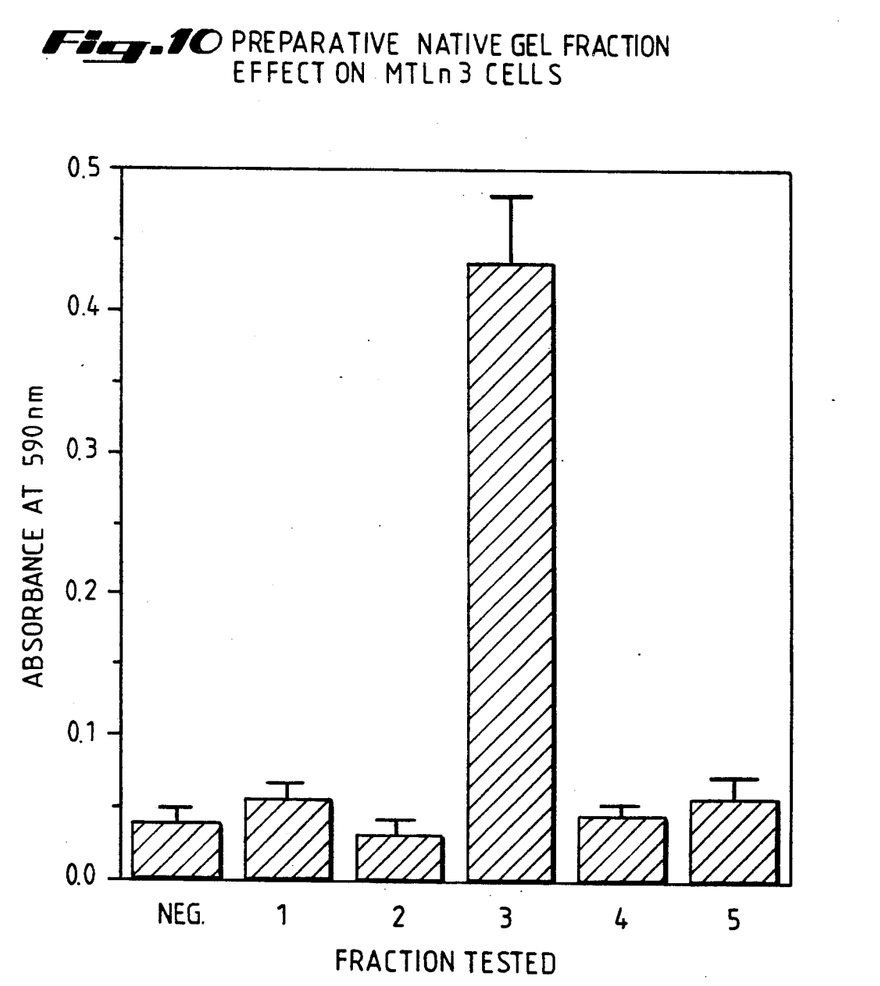
FIG. 10 shows the results obtained when electroeluted proteins from FIG. 9B were assayed. Assays were performed and quantitated using MTLn3 cells as described previously. The number below each bar indicates the protein band from the gel which was added into the cultures. Bars represent the mean ± SD from four wells.
Figure 11:
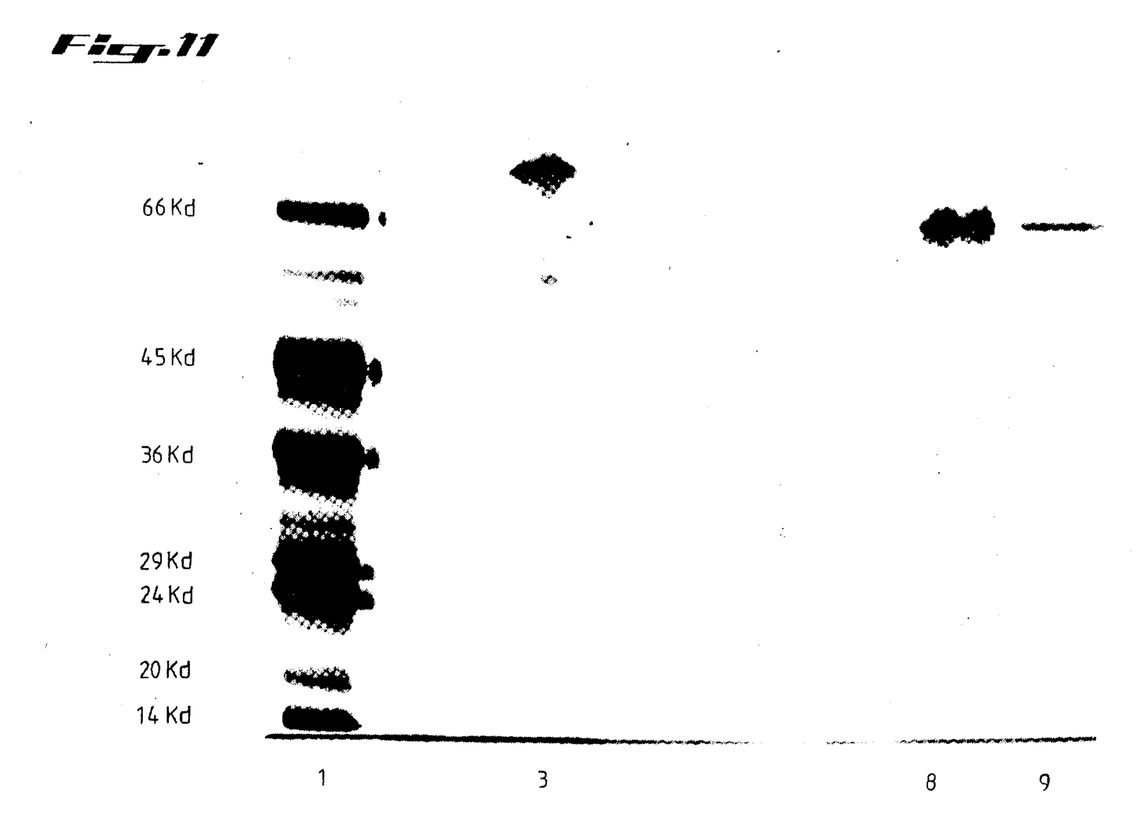
Figure 12:
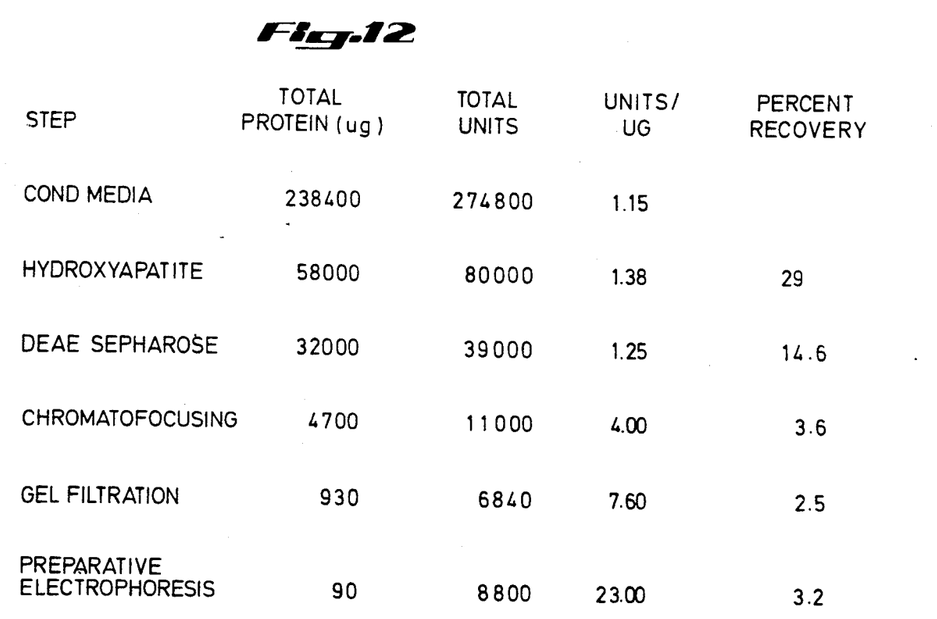
FIG. 12 shows purification data obtained from a recent LGF-1 purification using rat lung conditioned media as a source of activity. As with many protein isolation protocols, a large loss of total activity is seen during the purification process.

The following discussions relating to purification of growth factors is in the terms of the preferred embodiments of this invention, which represent the best mode known to the inventors at the time of this application.

EXPERIMENTAL PROCEDURES DEMONSTRATING BIOLOGICAL ACTIVITY OF THE LUNG GROWTH FACTOR

The activity of peptide growth factors derived from lung tissue is exemplified by induction of lung metastasizing tumor growth. The in vitro assay for lung growth factor activity uses mammary adenocarcinoma—the parental cells of which were designated MTPa and a highly metastatic cell line designated MTLn3 as described by Neri, et al. J. Nat'l. Cancer Inst. 68, 507–517 (1982). In brief, the cultured target cells are first exposed to growth factor. The degree of cell growth activity was measured by use of a colorimetric crystal violet cell staining assay described by Gillies, et al.

In addition, MCF-1 human mammery adenocarcinoma cell line isolated by Soule et al. (J. Nat. Cancer Inst. 51:1409–1413, 1973) can be used in the growth assays. The cell line is maintained in a 5% $CO_2$ humidified atmosphere in DME:F12 (1:1) media containing 10% v/v fetal calf serium. Growth assays using MCF-7 cells can be performed in the same manner as those for MTLn3 cells described below with the exception that DME:F12 media is used in place of alpha MEM.

CULTURES

The rat 13762NF mammary adenocarcinoma cells were established in culture from the parental cells MTPa as described by Neri, et al. A high lung metastasizing subline of these cells was isolated and classified as the MTLn line and this was further cloned to yield line MTLn3 of high spontaneous metastatic potential as described by Neri, et al., J. Nat'l. Cancer Inst. 68:507–517, 1982. In culture, under low serum conditions, MTLn3 cells demonstrate an enhanced growth response towards rat and porcine lung conditioned media. The response of low metastatic MTPa and MTC cells is much lower. The MTLn3 cell line is maintained in culture in 5% $CO_2$ humidified air at 37° C. in alpha MEM containing 10% v/v fetal calf serum. Frozen stocks of the cell line are kept in media containing 10% v/v DMSO at −135° C. Cultures are routinely started from frozen stocks to ensure that cells of low passage number (<25) are used for all assays. The line has been tested and shown to be mycoplasma free.

GROWTH FACTOR ASSAY METHODS

Rat MTLn3 or human MCF-7 cell cultures were set up in 96 well plates at a density of 2,000 cells per well. Initial plating was performed using alpha-MEM containing 1% (v/v) fetal calf serum. Twenty-four hours post-plating, the wells were washed with alpha-MEM. One hundred microliters of alpha-MEM containing 0.3% fetal calf serum was then placed into all the wells. Twenty microliters of lung growth factor-containing media or media fraction was placed into the test wells, and 20 microliters of control solution was placed into corresponding negative control wells. All controls or tests were performed in sextuplicate (B-G wells on a given row of a microtiter plate). Four days after application of the fractions to be tested, the cells in each well were quantitated using a colorimetric crystal violet cell staining assay as described by Gillies, et al. Anal. Biochem. 159:109–113, 1986. Dose response curves are then constructed and fit so that the activity fractions can be ascertained in terms of units. One unit of growth stimulating activity (gsa) is defined as the amount of material required to double the number of cells when compared to a corresponding negative control over a 4 day period. All absorbance readings obtained in the assay are converted to gsa units for activity expression on the chromatographs.

The following examples describe the purification schemes for lung growth factor of the present invention as well as the characterization of that factor.

EXAMPLE 1

Purification of the Lung Derived Growth Factor (LGF1)

The purification of the lung derived growth factor was carried out as follows:

Step 1: Rat lungs from freshly killed animals were perfused with 25 mM HEPES, 0.15M NaCl, 0.28% weight by volume sodium citrate at a pH of 7.5 prior to excision. Following perfusion with the described solution, the whole rat lungs were dissected free of the major bronchioles and then washed in sterile 25 mM HEPES, 0.15M NaCl (pH 7.5) and minced with a food processor until uniform pieces of 1–2 mm cubes were obtained. The pieces were washed extensively with 3–4 liters of the HEPES buffered saline solution and were placed in DME/F12 (1:1) culture media containing 100 mg per liter penicillin and 100 mg per liter streptomycin at a volume ratio of 4:1 (medium:tissue) in roller bottles and rotated at 37° C. for 12–24 hours. Media from these cultures was filtered free of the pieces by centrifugation at 5,000× g for 30 minutes.

Step 2: Hydroxylapatite (obtained from Bio Rad) was equilibrated with 10 mM potassium phosphate (pH 7.0). To the conditioned medium (900 ml; 405 mg protein) described above, 30 grams of equilibrated hydroxylapatite was added. The mixture was stirred for 30 minutes and the gel was collected on a Buchner funnel. The mixture was then washed with 400–500 ml of equilibration buffer and loaded onto a 2.5×20 cm column. Bound proteins were then eluted with a linear 500 ml 10–500 mM phosphate gradient (pH 7.0). Ten ml fractions were then collected at a flow rate of 0.5 ml/minute.

Step 3: The active material from Step 2 (200 ml; 326 mg protein) was dialyzed overnight using 4 liters of a 25 mM TRIS buffer (pH 8.5) and was applied to a 2.5×20 centimeter DEAE Sepharose (Sigma Chemical) column previously equilibrated with the same buffer. Bound proteins were eluted with a 400 ml linear 0 to a 0.5M KCl gradient in a 25 mM TRIS (pH 8.5). Eight ml fractions were collected at a low rate of 0.5 ml/minute.

Step 4: The active material from Step 3 (100 ml; 36.2 mg protein) was dialyzed overnight against 2 liters of a 25 mM phosphate buffer (pH 7.0) and was applied to a 1×10 cm concanavalin A-Agarose (Sigma Chemical) column previously equilibrated with the same buffer. Bound proteins were eluted with start buffer containing 0.2M α-methyl-mannoside.

Step 5: The bound fraction from Step 4 (20 ml; 1.22 mg protein) was concentrated to 2 ml using a pressurized Amacon apparatus equipped with a YM-5 membrane. The sample was applied to a 2.5×50 cm Sephacryl S-200 column. The column was equilibrated and run at a flow rate of 20 ml per hour with a 50 mM potassium phosphate buffer at a pH of 7.0 which contained 0.2 molar KCl. Five ml fractions were collected.

Step 6: The active fractions from step 5 (20 ml; 0.4 mg protein) were then pooled and made 1.7M in ammonium sulphate. The fraction was then applied at a flow rate of 0.5 ml per minute to a 0.5×5 cm phenyl superose fast protein liquid chromatography column (Pharmacia) previously equilibrated with the sample solvent. Bound proteins were eluted from the column using a 30 ml linear 1.7-0.0M ammonium sulfate gradient in a 20 mM potassium phosphate solution with a pH of 7.0. Two ml fractions were collected at a flow rate of 0.5 ml per minute.

A number of chromatographic techniques other than the 5 shown in the figures have since been utilized to purify LGF-1. These include FPLC anion exchange using a Mono-Q column, dye affinity chromatography using Cibacron blue F3GA-agarose, chromatofocusing, and preparative native gel electrophoresis. The two most useful techniques have been the latter two, described below.

For chromatofocusing, an LGF-1 sample is dialyzed overnight against 25 mM ethanolamine, pH 9.5 containing 2% w/v sorbitol and 0.05% w/v $NaN_3$. The sample is applied at a flow rate of 0.5 ml/min to a 1.0×20 cm column of Polybuffer Exchanger 94 equilibrated with the dialysis buffer. Bound proteins are eluted with 100 ml of a 1:10 dilution of Polybuffer 96, pH 6.0, containing 2% w/v sorbitol, and 0.05% $NaN_3$ at a flow rate of 0.5 ml/min. Recovered fractions are assayed for activity and their pH is determined. LGF-1 activity has been seen to elute at a pH of 6.9-7.0.

Native gel electrophoresis was accomplished using the procedure outlined by Chrambach and Jovin, Electrophoresis 4:190-204, 1983. The active fraction from the size exclusion chromatography step described above was concentrated to a volume of 0.5-1.0 ml and dialyzed against 0.369M. Tris, 0.166M HCl, 5% w/v sorbitol, 2% CHAPS, 0.001% bromophemol blue.

The gel used for native gel electrophoresis was comprised of 20 ml 5% w/v sorbitol, 0.2% CHAPS; 10 ml 4× gel buffer (1.47M Tris, 0.6632M HCl); 10 ml acrylamide concentrate (40% w/v acrylamide, 1% w/v bisacrylamide); 20 ul TEMED; 100 ul 10% w/v ammonium persulfate. The gel was cast in a LKB system 2001 vertical electrophoresis unit and pre-electrophoresed at 50 mA constant current for 1 hour using an anolyte consisting of 2.42g Tris, 10 ml 1N HCL per liter and a catholyte consisting of 1.5 g glycine and 10 ml 1N KOH per liter.

The concentrated sample is then applied to the gel and electrophoresed at 50 mA constant current until the indicator dye (bromophenol blue) is 1 cm from the bottom of the gel. The gel is then removed and stained using Diversified Biotech (Newton Centre, Mass.) quick stain using the procedure outlined by Leblanc and Cochrane, Anal. Biochem. 161:172-175, 1987.

The background gel stains a uniform blue and the proteins appear as a clear band. The protein containing regions were then sliced out and individually electroeluted using a Schliecher and Schuell (Keene, N.H.) elutrap device. The device was placed in a Bio Rad DNA sub cell electrophoresis chamber containing an elution buffer of 60 mM Tris, 40 mM CAPS (pH 9.4). Samples were eluted overnight at 20 mA constant current. Eluted proteins were harvested and tested for growth promoting activity.

CHARACTERIZATION OF THE GROWTH FACTOR

The growth factors of this invention are large glycoproteins. As determined by SDS-PAGE electrophoresis, the lung factor (LGF1) has a molecular weight of 66,000. When reduced, the apparent molecular weight increases to 72,000 to 74,000.

Characterization of the material which did not bind to Concanavalin-A agarose has been performed. The growth promoting activity for MTLn3 cells of this fraction was further purified by size exclusion chromatography and preparative native gel electrophoresis. The elution volume from the size exclusion column was identical to that of Con-A binding LGF-1. Analysis of the non concanavalin-A binding active protein (eluted from the native gel step) by SDS-PAGE followed by silver staining indicated that it possessed the same molecular weight as concanavalin-A binding LGF-1. It also behaved similarly to concanavalin-A binding LGF-1 when exposed to reducing conditions. LGF-1's which do and do not bind to Concanvalin-A appear to be the same proteins which merely differ slightly in glycosylation.

Purification of the growth factors using native gel electro phoresis and chromatofocusing have also helped to further define the growth factors of this invention.

The native gel electrophoresis was accomplished as described above. Visualized bands were cut out and the protein was electroelected. These bands were then assayed for activity using the method described above.

The protein exhibiting activity was then re-electrophoresed on an analytical SDS-PAGE gel. Silver staining of the gel reveal one protein band which appeared identical to the band recovered during the above described purification technique. Chromatofocusing of this protein has shown the pI of LGF1 to be 6.9 to 7.0.

The specific activity of LGF-1 as measured using the above assay growth stimulating activity is 23,000-25,000 units/mg protein. One unit of activity is the amount of LGF-1 required to double the number of MTLn3 cells in culture over a 4 day period.

No other sources of growth stimulating activity for MTLn3 cells other than LGF-1 were observed in lung conditioned media. No other major well defined peaks of activity were seen in any chromatographic procedure. The loss of total LGF-1 activity seen during purification is due to inactivation of a percentage of LGF-1 molecules and not due to the elimination of other growth factors from the conditioned media.

MITOGENIC ACTIVITY

The mitogenic activity of LGF1 against various target tissues was studied. The various target cells were cultured and exposed to LGF1 as described in the assay method discussion above. Increase in cell number over controls was quantitated using a crystal violet assay or a Coulter Counter.

LGF1 has been found to posses mitogenic activity for the highly lung metastasizing MTLn3 rat mammary adenocarcinona cell line but not for the low metastasizing MTPa parent line. The growth factor also stimulate the growth of MCF7 human mammary adenocarcinona cells and RAW117 murine lymphosarcoma cells.

No difference in effect was seen when comparing results from RAW117-P cells (low lung metastasizing) to those obtained when RAW117-L17 (high lung metastasizing) cells were used as targets.

The factor has some activity on highly metastatic murine B16F10 melanoma cells, however, this is much less than that seen with the MTLn3, MCF7 or RAW117 murine cell lines. No growth promoting effect was observed when human A375 or SH4 melanoma cell lines were used as targets.

UTILITY

The basic findings of this invention is that there is a specific high molecular weight glycoprotein growth factor involved in lung tumor cell growth in experimental animals and humans. This growth factor has been isolated in substantial amounts from normal mammalian lung target tissues. These activities have been shown to share many common biological properties.

Since the activities thus far isolated factors all show a potent growth factor activity with lung metastasizing cells and since relatively large amounts of these factors can be purified, the use of these activities and the treatment and diagnosis of lung cancers is an important application of our research.

Polyclonal and monoclonal antibodies to these growth factors can be used to develop specific radio immunoassay (RIA) methods of measurement for screening plasma and urine samples of patients suspected of having these tumors. Screening methods to determine individuals at potentially greater risk of expressing this type of cancer than the general population can be developed. Human monoclonal antibodies to the growth factor or their cell binding proteins are potential therapeutic reagents which can be used to eliminate the mitogenic activities from the circulation or the immediate microenvironment of the tumors. Since continual production of tumor cell growth factors is known to occur, the RIA method of measuring plasma concentration may serve as an important monitor for the effectiveness of chemotherapy protocols or radiation treatments.

Labeled antibodies, (second antibodies) can be used in laboratory pathology for diagnostic examination of biopsy tissues to determine the increased binding of the growth factor by metastatic tumor cells over the substantially lower concentrations found in non-metastatic tumor cells.

The antibodies according to the invention can be prepared in a variety of ways known in the art, depending upon whether monoclonal or polyclonal antibodies are desired. For polyclonal antibodies, a typically domestic animal, is hyperimmunized with antigen and the blood collected shortly after repeat immunizations in the gamma globulin isolet. Suitable methods for preparing polyclonal antibodies are described in the Handbook of Experimental Immunology, 3rd Edition, Weir, Editor, Blackwell Scientific Publications, Oxford in London, 1978.

For monoclonal antibodies, a small animal, typically a mouse or rat, is hyperimmunized with antigen, the spleen removed and the lymphocytes fused with a myeloma cells in the presence of a suitable fusion promoter. The resulting hybrid cells or hybridomas are screened to isolate individual clones, each of which secrete a single antibody species to the antigen. The individual antibody species obtained in this way are the product of a single B cell from the immune animal generating a response to a specific antigenic site recognized on the immuno genic substance. The general process for obtaining monoclonal antibodies, including those according to the invention, is described by Kohler and Milestein, Nature, 256:459-497, 1985. The growth factor peptides and antigenic oligopeptides, that is antigenic peptide fragments of the growth factor peptide of this invention, used to produce antibodies (both polyclonal and monoclonal) may be employed directly in the immunization procedure or they may be bound to suitable carrier-protein using methods known in the art, for example, see U.S. Pat. No. 4,341,761 to Ganfield, et al. Use of a carrier protein is particularly preferred when the immunization is carried out using the antigenic oligopeptides of this invention.

The antibodies according to the invention may be used in a variety of ways. In a preferred application, they may be used for diagnosis of malignancy or other proliferative diseases. In instances where antigen may be found in a physiological fluid or at a concentration differential only when a malignancy or other proliferative disease exists, the physiological fluid such as serum, urine, sputum, plasma, whole blood or cerebral spinal fluid may be assayed. Antibodies employed in assays may be labeled or unlabeled. Unlabeled antibodies may be employed in agglutinaton; labeled antibodies may be employed in a variety of assays, employing a wide variety of labels such as radionuclides, enzymes, fluorescers, enzymes substrates or cofactors or the like. These techniques are amply defined in the literature and examplarary assays may be found in U.S. Pat. Nos. 3,817,834; 3,395,074; 4,233,402 and 4,318,980 and is illustrative.

For purposes of therapy, either xenogenic or allogeneic antibodies may be employed depending upon the nature of the treatment and whether the foreign antibodies will induce an immune response. The literature has described a number of ways of making human antibodies, where it has been found that mouse or other mammalian antibodies are not satisfactory. The antibodies may be used in a wide variety of ways. By employing LGF1 antibodies or antibodies against a LGF1 receptor, one may induce lyses through natural compliment process. Alternatively, the lysing portion of the toxin may be joined to the antibodies particularly a Fab fragment. The antibodies may be bound to liposomes for directing the liposomes to the malignant cells to become ingested by the cells by merging the membranes. Other labels may also be bound to the antibodies such as radionucleides, fluorescers, enzymes and the like. By inducing the antibodies in vivo, the antibodies will direct the label to the malignant cell, where the presence of malignancy may be diagnosed or treated.

The formulation of the antibodies will vary widely depending upon the nature of the label, the purpose of the antibodies, the site to which the antibodies are to be directed, and the like. Usually, the antibodies will be formulated in a physiologically acceptable carrier, e.g. saline or phosphate buffer saline, and injected into the host when possible at the desired site and when this is not possible, into the circulating system such as blood.

In some techniques, it will be useful to label the antigen and fragment thereof rather than the antibody and have a competition between the labeled antigen and antigen in the sample for the antibody. In this situation, it is common to provide kits which have the combination of the labeled antigen or labeled fragments and the antibody in amounts which provide for optimum sensitivity and accuracy. In other situations, it is desirable to have a solid support where either the antigen or antibody is bound. A polyepitopic antigen can serve as a bridge between the antibody bound to a support and labeled antibody in the assay medium. Alternatively, one may have a competition between labeled antigen and any antigen in the sample for a limited amount of antibody.

Where the antigen may not be found in physiological fluid or detection there is not a diognostic of malignancy or other proliferative diseases, then the cells of interest will have to be isolated and the cells assayed for the presence of LGF1 or the LGF1 receptor where LGF1 receptor antibodies are used. For detecting the antigen, the tissue sample may have to be lysed by conventional methods, e.g. base, detergents or the like, cellular debris separated by filtration or centrifugation and the filtrate or supernatant isolated and assayed.

In addition to these uses of the growth factor and antibodies to these activities, the growth factor will be used to isolate the cell surface receptor proteins which provide another valuable approach to therapy. Human monoclonal antibodies to the growth factor receptor can be used to block growth factor action and hence provide a highly specific means for inhibiting further tumor growth. This approach to tumor therapy may avoid many of the problems of conventional cancer treatement which often have debilitating side effects.

The LGF1 can be used to isolate the cell surface receptors by the folowing method. First, LGF1 is immobilized. This can be accomplished by binding LGF1 to cyanogen bromide activated agarose. Next, the target cell plasma membranes are isolated. One method for this is the use of differential centrifugation and sucrose density centrifugation. The cell membranes are then solubilized and passed over the immobilized LGF1 followed by a buffer wash. The receptors will bind to the LGF1. The LGF1 receptor can then be eluted with a buffer containing a high salt concentration.

Methods and compositions employing LGF1 are also afforded for treatment of cancer or other proliferative diseases and for therapies wherein growth promotion is beneficial e.g. wound healing and ulcer therapy. These therapeutic compositions comprise effective amounts of the indicated peptides in admixture with pharmaceutically acceptable carriers. In particular, pharmaceutical compositions that contain the peptides of the invention as an active ingredient will normally be formulated with an appropriate solid or liquid carrier depending upon the particular mode of administration being used. For instance, parenteral formulations are usually injectable fluids that are pharamceutically and physiologically acceptable fluids such as physiological saline, balanced salt solutions, or the like as a vehicle. Oral formulations on the other hand may be solid e.g. tablet or capsule or liquid solutions or suspensions.

In the therapeutic methods of the invention, the peptides may be administered to humans in various manners such as orally, intravenously, intramuscularly, intraperitonelly, intranasally, intradermally, insubutaniously. The particular mode of administration and dosage regime will be selected by the attending physician taking into account the particulars of the patient, the nature of the treatment required and/or the diesase and the disease state involved. For instance, damages tissue from wounds is usually treated by daily or twice daily doses over a few days to a few weeks whereas tumor or cancer treatment involves daily or multi daily doses over months or years. The glycopeptide therapy of the invention may be combined with other treatments and may be combined or used in association with other chemotherapeutic or chemopreventive agents for providing therapy against proliferative diseases, neoplasms, or other conditions against which they are effective.

The growth factor of this invention can also be used to induce a burst of tumor cell growth increasing the effectiveness of cytoxic agents. Most cytoxic agents are only effective against cells in the growth phase. It has been observed that when growth factors are used to induce an increase in growth activity immediately before the administration of a cytoxic agent, the effectiveness of the cytoxic agent is significantly increased. (Nicolson & Lotan, Clin. Exp. Met. 4:231–236, 1986).

Finally, inactive fragments of LGF1, for example, the 39,000 dalton and 29,000 dalton fragments which result from cyanogen bromide cleavage or inactivated LGF1 can be used to bind to LGF1 receptors. This would reduce target cell response to LGF1 by competing with normal LGF1 for the receptor sites on the target cells.

While the invention has been described interms of the preferred embodiments constituting the best mode known to applicants at the time of this application, various changes may be made in the invention without departing from the scope thereof which is defined by the following claims.

What we claim is:

1. A protein growth factor for epithelial cells derived from lung tissues, characterized by:
    a molecular weight of approximately 66,000 daltons as determined by SDS PAGE electrophoresis under nonreducing conditions;
    a molecular weight of between 72,000 and 74,000 daltons as determined by SDS PAGE electrophoresis when said growth factor is in the reduced state;
    a pI of 6.9 to 7.0;
    stability of pHs of 7.0 to 9.5;
    being a glycoprotein;
    a specific activity of between 23,000 to 25,000 growth stimulating activity units per mg of protein; and
    exhibiting mitogenic activity in high metastasizing epithelial cell lines and substantially no mitogenic activity in low metastasizing epithelial cell lines.

2. The growth factor of claim 1 wherein said lung tissue is porcine lung tissue.

3. The growth factor of claim 1 wherein said lung tissue is rat lung tissue.

4. The growth factor of claim 1 wherein said lung tissue is human lung tissue.

5. A polyclonal or monoclonal antibody which recognize protein growth factor of claim 1, 2, 3, or 4.

6. A diagnostic reagent for detecting the presence of growth factors in biological sample comprising a monoclonal or polyclonal antibody which recognize the protein growth factor of claim 1, 2, 3, or 4 together with an inert diluent.

* * * * *

UNITED STATES PATENT AND TRADEMARK OFFICE
CERTIFICATE OF CORRECTION

PATENT NO. : 5,164,489

DATED : November 17, 1992

INVENTOR(S) : Nicolson et al

It is certified that error appears in the above-identified patent and that said Letters Patent is hereby corrected as shown below:

At column 3, line 47, "7 0" should instead read --7.0--.

At column 3, line 58, "ilustrate" should instead read --illustrate--.

At column 3, line 59, "ines" should instead read --lines--.

At column 12, line 21, "interms" should instead read --in terms--.

In claim 1, at column 12, line 38, "stability of" should instead read --stability to--.

Signed and Sealed this

Sixteenth Day of November, 1993

Attest:

BRUCE LEHMAN

*Attesting Officer*     *Commissioner of Patents and Trademarks*